US012075842B2

(12) United States Patent
Stockall et al.

(10) Patent No.: US 12,075,842 B2
(45) Date of Patent: Sep. 3, 2024

(54) CONFIGURING A PERSONAL COMPUTING DEVICE FOR COMMUNICATION WITH AN AEROSOL GENERATION DEVICE

(71) Applicant: JT International S.A., Geneva (CH)

(72) Inventors: Adrian Peter Stockall, Grand-Saconnex (CH); Magd Kudama Al Mudaris, London (GB); Jonathan Ruiz Peinado, London (GB)

(73) Assignee: JT International S.A.

( * ) Notice: Subject to any disclaimer, the term of this patent is extended or adjusted under 35 U.S.C. 154(b) by 34 days.

(21) Appl. No.: 17/609,282

(22) PCT Filed: Mar. 31, 2020

(86) PCT No.: PCT/EP2020/059108
§ 371 (c)(1),
(2) Date: Nov. 5, 2021

(87) PCT Pub. No.: WO2020/229045
PCT Pub. Date: Nov. 19, 2020

(65) Prior Publication Data
US 2022/0211119 A1    Jul. 7, 2022

(30) Foreign Application Priority Data
May 10, 2019   (EP) .................................... 19173859

(51) Int. Cl.
*A24F 40/65*       (2020.01)
*H04M 1/72412*   (2021.01)
*H04W 4/80*       (2018.01)

(52) U.S. Cl.
CPC ......... *A24F 40/65* (2020.01); *H04M 1/72412* (2021.01); *H04W 4/80* (2018.02)

(58) Field of Classification Search
CPC ...... A24F 40/65; H04W 4/80; H04M 1/72412
See application file for complete search history.

(56) References Cited

U.S. PATENT DOCUMENTS

| 8,639,873 B1 | 1/2014 | Jevans et al. |
| 9,942,164 B2 | 4/2018 | Yasunaga et al. |
| (Continued) | | |

FOREIGN PATENT DOCUMENTS

| CA | 3046851 A1 | 7/2018 |
| CN | 103914013 A | 7/2014 |
| (Continued) | | |

OTHER PUBLICATIONS

Bluetooth, "Bluetooth Core Specification 5.0," published on Dec. 6, 2016, pp. 1-2822, available online at: https://www.bluetooth.com/specifications/specs/core-specification-51.

(Continued)

*Primary Examiner* — David Bilodeau
(74) *Attorney, Agent, or Firm* — Lerner David LLP

(57) ABSTRACT

A method of configuring a personal computing device for communication with an aerosol generation device involves a Progressive Web Application, PWA. A native application launches a web browser on the personal computing device and the web browser launches the PWA. The native application provides a resource to the web browser, which resource causes the web browser to process a call received by the web browser from the PWA intended for the aerosol generation device by directing a command based on the call to the native application. The command allows the native application to cause the personal communication device to communicate with the aerosol generation device over the short-range wireless communication connection.

28 Claims, 8 Drawing Sheets

(56) References Cited

U.S. PATENT DOCUMENTS

| | | | |
|---|---|---|---|
| 10,039,327 | B2 | 8/2018 | Cameron et al. |
| 10,334,885 | B2* | 7/2019 | Baker .................... A24F 40/50 |
| 10,440,517 | B2* | 10/2019 | Baker .................... A61M 15/06 |
| 10,567,946 | B2* | 2/2020 | Baker .................... H04W 84/18 |
| 10,630,777 | B2* | 4/2020 | Baker .................... H04W 4/80 |
| 2009/0300596 | A1 | 12/2009 | Tyhurst et al. |
| 2013/0340775 | A1 | 12/2013 | Juster et al. |
| 2014/0157135 | A1 | 6/2014 | Lee et al. |
| 2014/0345633 | A1 | 11/2014 | Talon et al. |
| 2015/0095457 | A1 | 4/2015 | Goda et al. |
| 2015/0224268 | A1 | 8/2015 | Henry et al. |
| 2015/0281869 | A1 | 10/2015 | Ramachandran et al. |
| 2016/0182604 | A1 | 6/2016 | Ensign et al. |
| 2016/0219933 | A1 | 8/2016 | Henry, Jr. et al. |
| 2016/0219938 | A1 | 8/2016 | Mamoun et al. |
| 2016/0278435 | A1 | 9/2016 | Choukroun et al. |
| 2016/0337362 | A1 | 11/2016 | Cameron |
| 2016/0345631 | A1 | 12/2016 | Monsees et al. |
| 2017/0014582 | A1 | 1/2017 | Skoda |
| 2017/0034127 | A1 | 2/2017 | Singleton, IV et al. |
| 2017/0136193 | A1 | 5/2017 | Cameron |
| 2017/0273358 | A1 | 9/2017 | Batista et al. |
| 2017/0339250 | A1 | 11/2017 | Momchilov et al. |
| 2018/0286207 | A1 | 10/2018 | Baker et al. |
| 2018/0286208 | A1 | 10/2018 | Baker et al. |
| 2018/0289074 | A1 | 10/2018 | Tremblay |
| 2019/0065217 | A1 | 2/2019 | Girdhar et al. |
| 2019/0124401 | A1* | 4/2019 | Lentner .............. H04N 21/4856 |
| 2019/0165998 | A1 | 5/2019 | Qiu |
| 2019/0261687 | A1 | 8/2019 | Wensley et al. |
| 2020/0042332 | A1* | 2/2020 | Trocki ................ G06F 9/44526 |
| 2020/0060347 | A1* | 2/2020 | Kersey .................... H04W 4/80 |
| 2020/0221778 | A1* | 7/2020 | Trzecieski .............. A24F 40/10 |
| 2021/0007413 | A1* | 1/2021 | Moloney ................ A24F 40/65 |
| 2021/0304903 | A1* | 9/2021 | Silva ........................ G16Y 40/35 |
| 2022/0211118 | A1* | 7/2022 | Stockall .................. H04W 4/18 |
| 2022/0211119 | A1* | 7/2022 | Stockall .................. H04L 67/02 |
| 2022/0279860 | A1* | 9/2022 | Stockall ................ H04L 9/3073 |

FOREIGN PATENT DOCUMENTS

| | | |
|---|---|---|
| CN | 103997921 A | 8/2014 |
| CN | 105095810 A | 11/2015 |
| CN | 105453598 A | 3/2016 |
| CN | 105785864 A | 7/2016 |
| CN | 106164958 A | 11/2016 |
| CN | 106165370 A | 11/2016 |
| CN | 106455705 A | 2/2017 |
| CN | 106535673 A | 3/2017 |
| CN | 106793835 A | 5/2017 |
| CN | 107609150 A | 1/2018 |
| CN | 107925685 A | 4/2018 |
| CN | 108338418 A | 7/2018 |
| CN | 108348001 A | 7/2018 |
| CN | 108429819 A | 8/2018 |
| CN | 108851237 A | 11/2018 |
| CN | 109072474 A | 12/2018 |
| CN | 109171023 A | 1/2019 |
| CN | 109324822 A | 2/2019 |
| CN | 109446455 A | 3/2019 |
| CN | 109561734 A | 4/2019 |
| EP | 3094064 A1 | 11/2016 |
| EP | 3214844 A1 | 9/2017 |
| EP | 3324601 A1 | 5/2018 |
| JP | 2002290606 A | 10/2002 |
| JP | 2014110635 A | 6/2014 |
| JP | 2017513137 A | 5/2017 |
| JP | 6289004 B2 | 3/2018 |
| JP | 2018041484 A | 3/2018 |
| JP | 2018509139 A | 4/2018 |
| JP | 2018538711 A | 12/2018 |
| WO | 2013100990 A1 | 7/2013 |
| WO | 2014195805 A2 | 12/2014 |
| WO | 2014199233 A2 | 12/2014 |
| WO | 2017055799 A1 | 4/2017 |
| WO | 2017055802 A1 | 4/2017 |
| WO | 2018033049 A1 | 2/2018 |
| WO | 2018069673 A1 | 4/2018 |
| WO | 2018125889 A1 | 7/2018 |

OTHER PUBLICATIONS

Communication of a notice of opposition for Application No. 19173828.5 dated Jun. 1, 2022, 47 pages.

Communication pursuant to Article 94(3) EPC for Application No. 20713685.4 dated Oct. 25, 2022, 6 pages.

Gash, D. "HTTP Caching," Published on Feb. 22, 2018, Updated Aug. 17, 2018, pp. 1-4, available online at: https://web.dev/performance-get-started-httpcaching-6/.

Leenheer, N. "An Introduction to WebBluetooth" [online] Feb. 13, 2019 pp. 1-12, Internet URL<https://www.smashingmagazine.com/2019/02/introduction-to-webbluetooth/>.

Search Report dated May 22, 2022 from the Office Action for Taiwanese Application No. 109115411 issued May 27, 2022, 1 page. [See p. 1, categorizing the cited references].

Search Report dated May 25, 2022 from Office Action for Taiwanese Application No. 109115412 issued May 30, 2022. (see p. 1, categorizing the cited references).

Shaked, U. "Start Building with Web Bluetooth and Progressive Web Apps" [online]?Aug. 26, 2016, pp. 1-13, URL<https://urish.medium.com/start-building-with-web-bluetooth-and-progressive-web-apps-6534835959a6>.

Sheppard, D., "Beginning Progressive Web App Development," Apress, Nov. 29, 2017, pp. 1-266, available online at: https://link.springer.com/book/10.1007/978-1-4842-3090-9.

International Search Report for Application No. PCT/EP2020/059104, dated Apr. 17, 2020, 3 pages.

Extended European Search Report for Application No. 19173828.5, dated Nov. 20, 2019, 3 pages.

International Search Report for Application No. PCT/EP2020/059108, dated Jun. 26, 2020, 4 pages.

Gazdecki et al, "Why Progressive Web Apps Will Replace Native Mobile Apps", Mar. 9, 2018 (Mar. 9, 2018). 5 pgs.

Hume et al., "Progressive Web Apps", In: "MEAP version 6", Jul. 25, 2017 (Jul. 25, 2017), Manning Publications. 187 pgs.

Search Report dated Feb. 6, 2023 from the Office Action for Chinese Application No. 202080031511.3 issued Feb. 7, 2023, 2 pages.

Search Report dated Oct. 9, 2023 from the Office Action for Chinese Application No. 202080031511.3 issued Oct. 16, 2023, 2 pages.

Search Report dated Nov. 24, 2023 from the Office Action for Chinese Application No. 202080031784.8 issued Nov. 28, 2023, pp. 1-2.

Search Report dated Mar. 5, 2024 from the Office Action for Chinese Application No. 202080031511.3 issued Mar. 26, 2024, 2 pages.

* cited by examiner

700

- 702 Launch PWA
- 704 Access browser storage of web browser comprising one or more consumer apparatus identifiers
- 706 Determine an aerosol generation device with which to communicate
- 708 Retrieve consumer apparatus identifier of to the selected aerosol generation device
- 710 Initiate short-range wireless communication connection between personal computing device and selected aerosol generation device

- 802 Receive configuration information regarding the functioning of aerosol generation device from aerosol generation device
- 804 Store configuration information in browser storage of the web browser
- 806 Determine connection to remote server is available
- 808 Transmit configuration information to the remote server

FIG. 8

CONFIGURING A PERSONAL COMPUTING DEVICE FOR COMMUNICATION WITH AN AEROSOL GENERATION DEVICE

CROSS-REFERENCE TO RELATED APPLICATIONS

The present application is a national phase entry under 35 U.S.C. § 371 of International Application No. PCT/EP2020/059108, filed Mar. 31, 2020, published in English, which claims priority to European Application No. 19173859.0 filed May 10, 2019, the disclosures of which are incorporated herein by reference.

FIELD OF THE DISCLOSURE

The present disclosure relates to configuring a personal computing device for communication with an aerosol generation device. The disclosure is particularly, but not exclusively, applicable to a short-range wireless communication connection between a personal computing device and an aerosol generation device, such as a personal inhaler device or an electronic cigarette (or e-cigarette).

BACKGROUND TO THE DISCLOSURE

The popularity and use of reduced-risk or modified-risk smoking devices, also known as electronic cigarettes, vaporisers or aerosol generation devices, has grown rapidly in the past few years. Such aerosol generation devices provide an alternative to traditional tobacco products, such as cigarettes, cigars, cigarillos, and rolling tobacco. They generally heat or warm an aerosolisable substance to generate an aerosol for inhalation, as opposed to burning tobacco as in conventional tobacco products.

Most aerosol generation devices incorporate some form of electronic control circuit, typically including a simple computer processor, allowing a user to control operation of the aerosol generation device. However, the control of the aerosol generation device is generally only performed locally, by a user directly interacting with the aerosol generation device itself, for example by the user operating buttons or other user controls on the aerosol generation device and interpreting the meaning of indicators, such as Light Emitting Diodes (LEDs), on the aerosol generation device. This limits the flexibility with which the aerosol generation device can be controlled. It also means that the manufacturer or supplier of the aerosol generation device has little interaction with the aerosol generation device once it is in the possession of the user. Software running on the device cannot easily be updated and use of the aerosol generation device cannot easily be monitored to improve the user experience.

Short-range wireless communication connections, such as Bluetooth®, are available to allow a consumer apparatus, such as an aerosol generation device, to communicate with a personal computing device. This type of connection can be exploited to allow the consumer apparatus to be controlled in a more sophisticated manner via the personal computing device.

Typically, the operating system of the personal computing device, sometimes alongside an appropriate driver, manages the short-range wireless communication connection, but does not in itself facilitate control of the consumer apparatus. Rather, dedicated applications that can run on the personal computer device are required in order to facilitate control of the consumer apparatus via the short-range wireless communication connection managed by the operating system. As many personal computer devices can only run a limited range of applications, significant difficulties can be encountered when seeking to provide a single application that runs on a range of different personal computer devices to facilitate control of the consumer apparatus, yet is able to access the short-range wireless communication connection managed by the different operating systems and/or the appropriate driver. This is due in part to the different operating requirements of different personal computer devices, such as personal computer devices with different operating systems, e.g. macOS®, Android® or Microsoft® Windows®. It is also due to restrictions put in place by manufacturers and suppliers of personal computing devices regarding the applications that they allow to be installed on their personal computing devices, for example with the Apple® App Store, Google® Play™ App Store or Windows® Store, each requiring applications to meet certain (different) criteria before being approved for inclusion in the store and hence made available to users.

The present disclosure seeks to overcome the problems outlined above.

SUMMARY OF THE DISCLOSURE

Aspects of the disclosure are set out in the accompanying claims.

According to a first aspect of the present disclosure, there is provided a method of configuring a personal computing device for communication with an aerosol generation device over a short-range wireless communication connection, the method comprising:
  a native application launching a web browser on the personal computing device;
  the web browser launching a progressive web application, PWA, on the personal computing device; and
  the native application providing a resource to the web browser, which resource causes the web browser to process a call received by the web browser from the PWA intended for the aerosol generation device by directing a command based on the call to the native application, the command causing the native application to cause the personal communication device to communicate with the aerosol generation device over the short-range wireless communication connection.

By providing a resource to the web browser, the native application may alter the functioning of the web browser or the PWA. In particular, this may allow the PWA to interact with the personal computing device, e.g. an operating system or a wireless communication controller of the personal computing device, in such a way as to control the short-range wireless communication connection directly.

Optionally, the resource comprises computer executable code defining operations of the web browser. The computer executable code may be JavaScript®.

Optionally, the command comprises computer executable code defining operations of the native application. This computer executable code may be Swift code.

Optionally, the resource is provided as an object of the web browser.

Optionally, the resource is provided in a Document Object Model of the PWA.

Optionally, the native application causes the personal communication device to communicate with the aerosol generation device over the short-range wireless communication connection by communicating with a wireless communication controller of the personal computing device.

Optionally, the short-range wireless communication connection is a Bluetooth® connection.

Optionally, the call is for initiating the short-range wireless communication with the aerosol generation device and in response to the call the native application is configured to return a consumer apparatus identifier received from the aerosol generation device to the web browser.

Optionally, the consumer apparatus identifier is a Media Access Control (MAC) address for the aerosol generation device.

Optionally, the method further comprises the web browser launching the PWA using files for the PWA downloaded from a web server or stored locally at the personal computing device, whereby even if the personal computing device does not presently have an internet connection, the PWA can still run provided the files for the PWA can be obtained from local storage on the device.

Optionally, the personal computing device is a mobile personal computing device. It may be a smartphone or tablet.

According to another aspect of the disclosure, there is provided a method of configuring a personal computing device for communication with an aerosol generation device over a short-range wireless communication connection, the method comprising:

a native application launching a web browser on the personal computing device;

the web browser launching a progressive web application, PWA, on the personal computing device;

the PWA causing the personal computing device to establish the short-range wireless communication connection with the consumer apparatus; and storing instructions and/or data for implementing one or more functions of the PWA in browser storage of the web browser, such that after the web browser has been closed and subsequently relaunched by the native application the web browser can retrieve the instructions and/or data for implementing the one or more functions of the PWA from the browser storage.

By storing information or files for running the PWA in the browser storage, the personal computing device may be advantageously configured for communication with the consumer apparatus. For example, the PWA can be launched from the files stored in the browser storage without a communication connection to a web server from which the files are generally available, e.g. the PWA may operate in an off-line mode. Similarly, the information enabling functioning of the PWA may be accessed at the time the PWA is launched, rather than waiting until a connection to the Internet is established or for the information to be retrieved from elsewhere.

Optionally, the instructions and/or data for implementing the one or more functions of the PWA comprise(s) computer executable code for running the PWA. The computer executable code for running the PWA may allow the web browser to launch the PWA when the personal computing device is not connected to the Internet.

Optionally, the instructions and/or data for implementing the one or more functions of the PWA comprise(s) information enabling establishment of the short-range wireless communication connection with the aerosol generation device. The instructions and/or data for implementing the one or more functions of the PWA may comprise a consumer apparatus identifier and the PWA causing the personal computing device to establish the short-range wireless communication connection with the aerosol generation device may comprise the PWA retrieving a consumer apparatus identifier for the aerosol generation device from the browser storage of the web browser.

Optionally, the PWA causing the personal computing device to establish the short-range wireless communication connection with the aerosol generation device comprises the PWA causing the native application to control the personal computing device to establish the short-range wireless communication connection using a/the consumer apparatus identifier for the aerosol generation device.

Optionally, the method further comprises:

causing the personal computing device to scan for one or more candidate aerosol generation devices using a short-range wireless communication protocol; and receiving a consumer apparatus identifier for each of the one or more candidate aerosol generation devices in the vicinity of the personal computing device.

Optionally, the scanning for the one or more candidate aerosol generation devices is initiated by the native application. Preferably, receiving the consumer apparatus identifier(s) for the one or more candidate aerosol generation device is performed by the native application.

Optionally, the method further comprises sending, from the native application to the PWA, the consumer apparatus identifier(s) for the one or more candidate aerosol generation devices.

Optionally, the PWA causing the personal computing device to establish the short-range wireless communication connection with the aerosol generation device comprises the PWA determining the aerosol generation device with which to establish the short-range wireless communication connection from the one or more candidate aerosol generation devices.

Optionally, determining the aerosol generation device with which to establish the short-range wireless communication connection comprises:

causing the personal computing device to display a list of the one or more candidate aerosol generation devices; and receiving a user selection of one of the one or more candidate aerosol generation devices as the aerosol generation device with which to establish the short-range wireless communication connection.

Optionally, causing the personal computing device to display the list of the one or more candidate aerosol generation devices on the personal computing device and receiving the user selection of one of the one or more candidate aerosol generation devices as the aerosol generation device with which to establish the short-range wireless communication connection is performed by the native application.

Optionally, the method further comprises receiving, at the personal computing device, from the aerosol generation device, information indicative of the functioning of the aerosol generation device via the short-range wireless communication connection.

Optionally, the method further comprises storing the information indicative of the functioning of the aerosol generation device in the browser storage of the web browser.

Optionally, the method further comprises the personal computing device transmitting the information indicative of the functioning of the aerosol generation device to a remote server.

Optionally, the method further comprises, prior to transmitting the information indicative of the functioning of the aerosol generation device to the remote server:

determining whether a communication connection to the remote server is established at the personal computing device, preferably by determining that the personal computing device has internet access; and in response to determining that the communication connection to the remote server is not established at the personal computing device, causing the communication connection to be set up between the personal computing device and the remote server, preferably by causing the personal computing device to access the Internet.

Optionally, the method further comprises sending, from the personal computing device to the aerosol generation device, information for the aerosol generation device via the short-range wireless communication connection, preferably wherein the information for the aerosol generation device comprises one or more settings for the aerosol generation device and/or a firmware update.

Optionally, the short-range wireless communication connection is a Bluetooth® connection and the consumer apparatus identifier is a Media Access Control, MAC, address.

Optionally, the method further comprises receiving, from the remote server, files for running the PWA.

Optionally, the personal computing device is a mobile personal computing device, preferably a smartphone or tablet.

According to another aspect of the disclosure, there is provided personal computing device configured for communication with an aerosol generation device over a short-range wireless communication connection, the personal computing device comprising a processor configured to cause the processor to carry out the method described above.

For example, the processor may cause:

a native application to launch a web browser on the personal computing device;

the web browser to launch a progressive web application, PWA, on the personal computing device;

the PWA to cause the personal computing device to establish the short-range wireless communication connection with the consumer apparatus; and storing instructions and/or data for implementing one or more functions of the PWA in browser storage of the web browser, such that after the web browser has been closed and subsequently relaunched by the native application the web browser can retrieve the instructions and/or data for implementing the one or more functions of the PWA from the browser storage.

In another example, the processor may cause:

a native application to launch a web browser on the personal computing device;

the web browser to launch a progressive web application, PWA, on the personal computing device; and the native application to provide a resource to the web browser, which resource causes the web browser to process a call received by the web browser from the PWA intended for the aerosol generation device by directing a command based on the call to the native application, the command causing the native application to cause the personal communication device to communicate with the aerosol generation device over the short-range wireless communication connection.

It can be appreciated that the methods can be implemented, at least in part, using computer program code. According to another aspect of the present disclosure, there is therefore provided computer software or computer program code adapted to carry out these methods described above when processed by a computer processing means. The computer software or computer program code can be carried by computer readable medium, and in particular a non-transitory computer readable medium, that is a medium on which computer code may be stored permanently, or until it is overwritten. The medium may be a physical storage medium such as a Read Only Memory (ROM) chip. Alternatively, it may be a disk, such as a Digital Video Disk (DVD-ROM), or a non-volatile memory card, e.g. a flash drive or mini/micro Secure Digital (SD) card. It could also be a signal such as an electronic signal over wires, an optical signal or a radio signal such as over a mobile telecommunication network, a terrestrial broadcast network or via a satellite or the like. The disclosure also extends to a processor running the software or code, e.g. a computer configured to carry out the methods described above.

According to another aspect of the disclosure, there is provided a personal computing device comprising:

storage storing the computer program product for carrying out the method;

a short-range wireless communication interface; and the computer processor operable to process the computer program product to carry out the method.

Use of the words "apparatus", "server", "device", "processor", "communication interface" and so on are intended to be general rather than specific. Whilst these features of the disclosure may be implemented using an individual component, such as a computer or a Central Processing Unit (CPU), they can equally well be implemented using other suitable components or a combination of components. For example, they could be implemented using a hard-wired circuit or circuits, e.g. an integrated circuit, and using embedded software.

The term "browser storage" means data stored in, by or in association with the web browser on the client/user device and which persists after the session ends or after the web browser stops its execution. One type of browser storage is known as "local storage". Data stored in browser storage or local storage is not automatically transmitted to the web server in every request or interaction with the server and cannot be written to directly by the server (unlike cookies). Local storage is distinguished from session storage, which is per-origin-per-window-or-tab and does not persist after the session is over, or the tab or window closed. Local storage is available, for example, in HTML5. The terms browser storage and local storage are intended to be general rather than specific, to include not just "local storage" as that term is used in HTML5 but also other equivalent forms of browser storage or local storage (e.g. other forms of web storage such as Indexed DataBase or Web SQL, etc.)

The term "aerosol" means a system of particles dispersed in the air or in a gas, such as mist, fog, or smoke. Accordingly the term "aerosolise" (or "aerosolize") means to make into an aerosol and/or to disperse as an aerosol. Note that the meaning of aerosol/aerosolise is consistent with each of volatilise, atomise and vaporise as defined above. For the avoidance of doubt, aerosol is used to consistently describe mists or droplets comprising atomised, volatilised or vaporised particles. Aerosol also includes mists or droplets comprising any combination of atomised, volatilised or vaporised particles. In preferred embodiments, the aerosol comprises a condensation aerosol which is formed by vapourising a liquid (preferably including an aerosol former liquid such as Vegetable Glycerin (VG), Propylene Glycol (PG) or a mixture thereof (PG/VG)) which then condenses to form a condensation aerosol comprising very small droplets of the vapourised liquid preferably having an indicative range of diameters between 0.5-7 microns and ideally where the maximum droplet size (for at least the vast majority of the droplets, e.g. up to about 99% of the droplets) is less than 10 microns.

As used herein, the term "aerosol generation device" or "electronic cigarette" may include a device configured to deliver a variable amount of aerosol to a user (especially a variable amount of aerosol per puff dependent upon things such as the settings of the device, the puff duration, or the puff intensity, of the user, etc.). The aerosol produced is preferably a condensation aerosol for inhalation. The device is preferably portable. Preferably the device is configured to dispense a variable amount of aerosol during a puff dependent upon the behavior of the user (e.g. a user who takes a long deep puff will cause the device to generate more aerosol during that puff than one who takes a short light puff).

It should be noted that the term "comprising" as used in this document means "consisting at least in part of". So, when interpreting statements in this document that include the term "comprising", features other than that or those prefaced by the term may also be present. Related terms such as "comprise" and "comprises" are to be interpreted in the same manner. As used herein, "(s)" following a noun means the plural and/or singular forms of the noun.

Each of the aspects above may comprise any one or more features mentioned in respect of the other aspects above.

Preferred embodiments are now described, by way of example only, with reference to the accompanying drawings.

BRIEF DESCRIPTION OF THE DRAWINGS

FIG. 7 is a flow diagram illustrating a method of later initiating the short-range wireless communication connection between the personal computing device and the aerosol generation device.

FIG. 8 is a flow diagram illustrating a method of collecting and transmitting information about the aerosol generation device to the remote server.

DETAILED DESCRIPTION OF PREFERRED EMBODIMENTS

Figure 1:
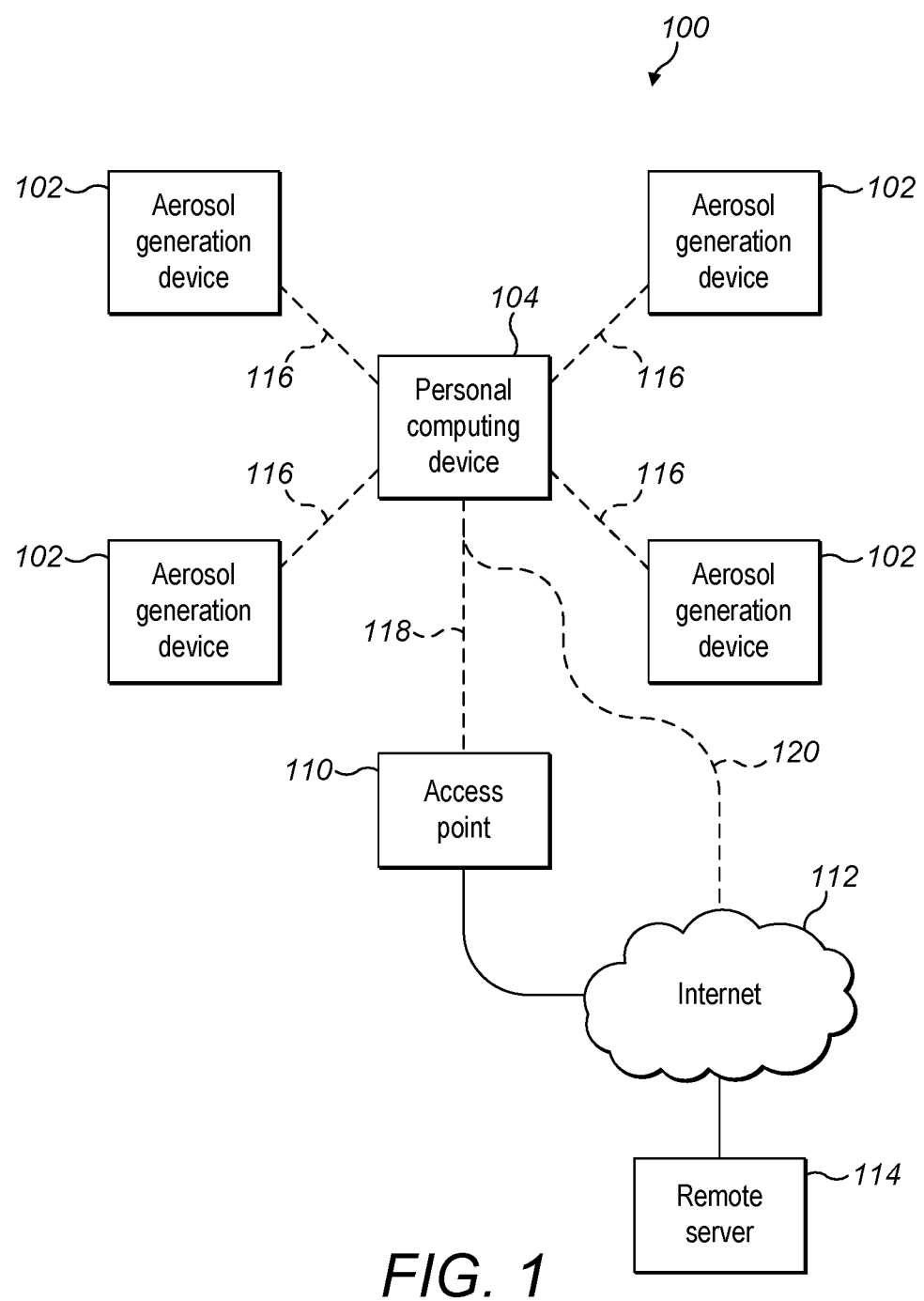
FIG. 1 is a schematic diagram of a communication network according to a preferred embodiment of the disclosure.

Referring to FIG. 1, according to a first embodiment, in a communication network 100 a personal computing device 104 is in communication with one or more aerosol generation devices 102 (each of which is a consumer apparatus). In the illustrated embodiment, the personal computing device 104 is potentially in communication with four aerosol generation devices 102. A communication link between the personal computing device 104 and each aerosol generation device 102 is a short-range wireless communication connection 116. In the present embodiment, this short-range wireless communication connection 116 is a Bluetooth® connection. In other embodiments, the short-range wireless communication connection 116 is a connection implemented using one or more of the Institute of Electrical and Electronics Engineers (IEEE) 802.11 standards (W-Fi®), an Infrared (IR) wireless connection, a ZigBee® connection or some other similar connection. In one particular embodiment, the short-range wireless communication connection is a Near-field Communication (NFC) connection. NFC employs electromagnetic induction between two loop antennas. NFC-enabled devices, e.g. the personal computing device 104 and the aerosol generation device 102, exchange information using a globally available unlicensed radio frequency band, e.g. the industrial, scientific and medical (ISM) band of 13.56 MHz. NFC communication is defined by the International Organization for Standardization (ISO) and the International Electrotechnical Commission (IEC) Joint Technical Committee (JTC). The ISO/IEC 18000-3 standard achieves rates ranging from 106 to 424 kbit/s. The reference to "short-range" in the context of the short range wireless communication connections 116 therefore means capable of being maintained over a few metres, for example up to around 100 metres but usually less than 10 metres and, indeed, in the context of NFC for example, less than 10 cm or even just up to 4 cm.

The personal computing device 104 is also in communication with a remote server 114 via the Internet 112. In the present embodiment, the personal computing device 104 is arranged to communicate with the Internet 112 via an access point 110. The personal computing device 104 is arranged to communicate with the access point 110 via another short-range wireless communication connection 118. This other short-range wireless communication connection 118 is a Wi-Fi® connection in the present embodiment. In other embodiments, the other short-range wireless communication connection 118 is a Bluetooth® connection, IR wireless connection, ZigBee® connection or some similar connection. In the present embodiment, the personal computing device 104 is also arranged to communicate with the Internet 112 via a cellular radio network link 120 using an appropriate communication standard, such as Global System for Mobile Communications (GSM), Universal Mobile Telecommunications System (UMTS) or Long-Term Evolution (LTE), to provide data communication. The personal computing device 104 typically selects to communicate with the Internet 112 from time to time via the other short-range wireless communication connection 118 and the access point 110 or via the cellular radio network link 120, depending upon availability and other criteria and preferences.

In the present embodiment, the personal computing device 104 is a mobile computing device, in particular a smartphone running the Android® operating system. In other embodiments, the personal computing device 104 is a smartphone, tablet computing device or laptop computer running any other type of operating system such as iOS, Linux or Windows for mobile OS. In most embodiments, the personal computing device 104 is arranged to communicate via the cellular radio network link 120 and as such the personal computing device 104 can be referred to as User Equipment (UE). In other embodiments, the personal computing device 104 is a desktop Personal Computer (PC) configured to communicate via the Internet 112 via a wired Ethernet connection. In such an embodiment, the Ethernet connection is effectively similar to the other short-range wireless connection 118, in that it connects, albeit via a fixed line or wired connection rather than a wireless one, to the access point 110, e.g. in the form of a broadband modem or the like, and thence on to the Internet 112.

Figure 2:
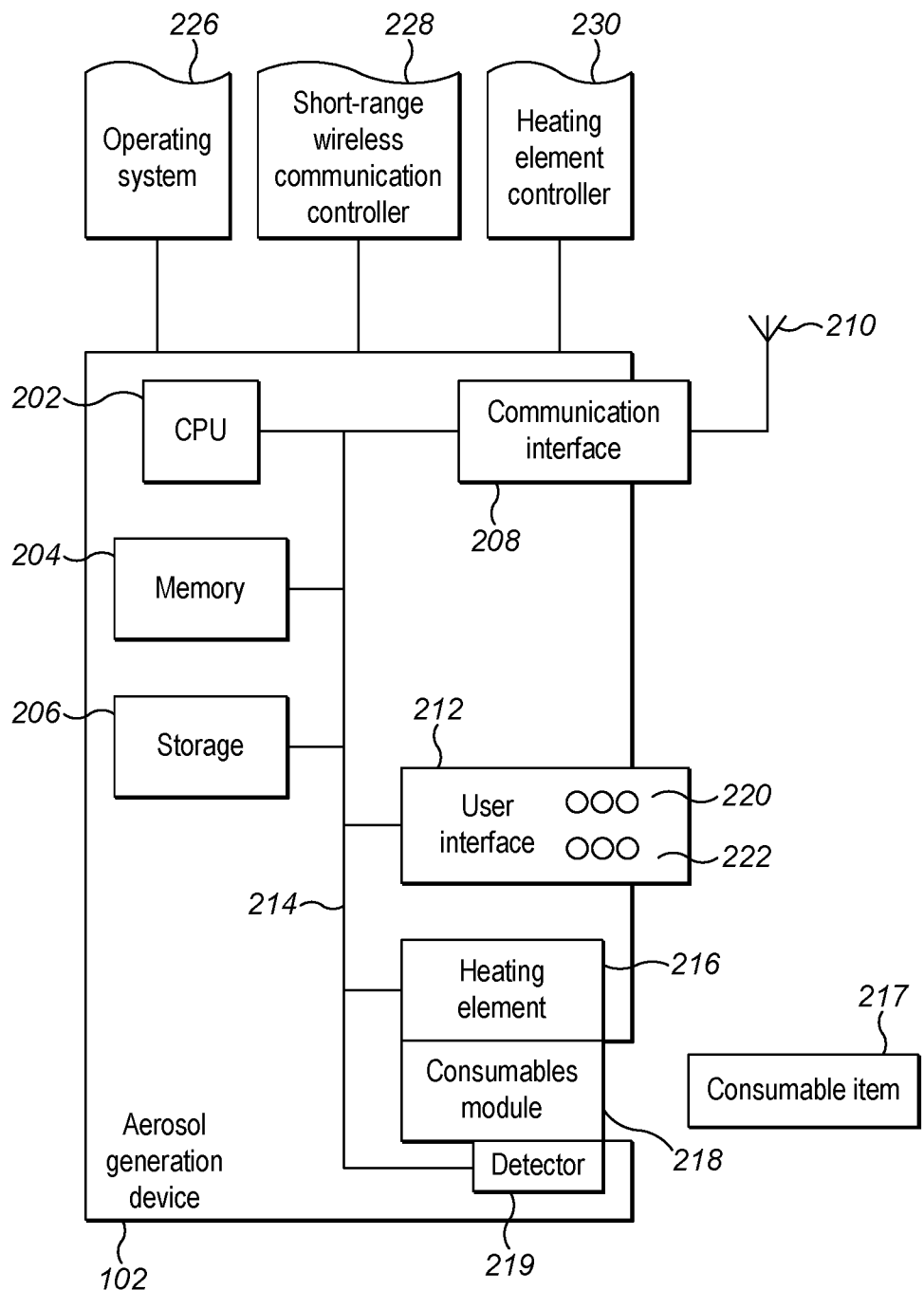
FIG. 2 is a schematic diagram of an aerosol generation device operating in the communication network.

Referring to FIG. 2, in common with a general electronic consumer apparatus, each aerosol generation device 102 comprises a Central Processing Unit (CPU) 202, memory 204, storage 206, communication interface 208, antenna 210 and a user interface 212 in communication with one another via a communication bus 214.

The aerosol generation device 102 also has aerosol generation components, in particular a heating element 216 and a consumables module 218 which includes, in the present embodiment, a detector 219 for detecting when a suitable consumable item 217 has been inserted into the consumables module 218. Note that in the present embodiment, the consumable item 217 is in the form of a tobacco rod or stick as described in greater detail below and includes a mouthpiece, e.g. a filter such as an acetate or through hole filter as commonly used in cigarettes. It should be noted, however, that several of the methods described below are applicable to other types of consumer apparatus, which typically have the computer related components but not the aerosol generation components of the aerosol generation device 102. It should therefore be understood that, in the context of those methods, the described aerosol generation device 102 is just one example of an appropriate consumer apparatus for use with the methods.

The CPU 202 is a computer processor, e.g. a microprocessor. It is arranged to execute instructions, e.g. in the form of computer executable code, and to process data, e.g. in the form of values and strings, including instructions and data stored in the memory 204 and the storage 206. The instructions and data executed by the CPU 202 include instructions for coordinating operation of the other components of the aerosol generation device 102, such as instructions and data for controlling the communication interface 208 and the user interface 212.

The memory 204 is implemented as one or more memory units providing Random Access Memory (RAM) for the aerosol generation device 102. In the illustrated embodiment, the memory 204 is a volatile memory, for example in the form of an on-chip RAM integrated with the CPU 202 using System-on-Chip (SoC) architecture. However, in other embodiments, the memory 204 is separate from the CPU 202. The memory 204 is arranged to store the instructions and data executed and processed by the CPU 202. Typically, only selected elements of the instructions and data are stored by the memory 204 at any one time, which selected elements define the instructions and data essential to the operations of the aerosol generation device 102 being carried out at the particular time. In other words, the instructions and data stored transiently in the memory 204 whilst some particular process is handled by the CPU 202.

The storage 206 is provided integrally with the aerosol generation device 102, in the form of a non-volatile memory. The storage 206 is in most embodiments embedded on the same chip as the CPU 202 and the memory 204, using SoC architecture, e.g. by being implemented as a Multiple-Time Programmable (MTP) array. However, in other embodiments, the storage 206 is an embedded or external flash memory, or such like. The storage 206 stores the instructions and data executed and processed by the CPU 202. The storage 206 stores the instructions and data permanently or semi-permanently, e.g. until overwritten. That is, the instructions and data are stored in the storage 206 non-transiently. Typically, the instructions and data stored by the storage 206 relates to instructions fundamental to the operation of the CPU 202, communication interface 208, user interface 212 and the aerosol generation device 102 more generally, as well as to applications performing higher-level functionality of the aerosol generation device 102.

The communication interface 208 supports short-range wireless communication, in particular Bluetooth® communication. The communication interface 208 is configured to establish the short-range wireless communication connection 116 with the personal computing device 104. The communication interface 208 is coupled to the antenna 210, via which antenna 210 wireless communications are transmitted and received over the short range wireless communication connection 116. It is also arranged to communicate with the CPU 202 via the communication bus 214.

The user interface 212 comprises a display 220 and input device 222. In this embodiment, the display 220 is a plurality of separate indicators, such as Light Emitting Diodes (LEDs). In other embodiments, the display 220 is a screen, such as a Thin-Film-Transistor (TFT) Liquid Crystal Display (LCD) display or an Organic Light Emitting Diode (OLED) display, or other appropriate display. The input device 222 is one or more user operable buttons, responsive to depression, toggling or touch by the user. The user interface 212, is arranged to provide indications to the user, under the control of the CPU 202, and to receive inputs from the user, and to convey these inputs to the CPU 202 via the communications bus 214.

The aerosol generation device 102 may be described as a personal inhaler device, an electronic cigarette (or e-cigarette), a vaporiser or vaping device. In one particular embodiment, the aerosol generation device 102 is a Heat-not-Burn (HnB) device. All of these devices generally heat or warm an aerosolisable substance to generate an aerosol for inhalation, as opposed to burning tobacco as in conventional tobacco products.

In more detail, the aerosol generation device 102 is configured to heat a consumable item 217 inserted into the consumables module 218, using the associated heating element 216 to produce an inhalable aerosol or vapour for a user to inhale. The consumables module 218, in the present embodiment, is intended to receive a consumable item 217 in the form of a rod which contains processed tobacco material (e.g. a crimped sheet or oriented strips of Reconstituted ToBacco (RTB) paper impregnated with a liquid aerosol former). The liquid aerosol former in the present embodiment comprises Vegetable Glycerin (VG) but may be a mixture of Propylene Glycol (PG) and VG or other humectants, e.g. vegetol (13 propanediol), the use of which in the present embodiment may be advantageous as it performs well in nicotine containing aerosol formulations over a range of different temperatures of the heating element; since the present embodiment provides the possibility for the user to adjust operating temperatures in a convenient manner the use of such humectants which perform well over a range of operating temperatures is beneficial. It should be noted that this advantage applies to all sorts of embodiments (e.g. liquid vaporising e-cigarettes as well as heat not burn type devices) and thus the advantageous use of vegetol is not limited to any particular type of aerosol generating device. In the present embodiment, the consumable item 217 uses pure VG, which does not contain any flavourings or nicotine. Instead, volatile flavourings and nicotine derived from the RTB are vapourised at the same time as the aerosol former and is entrained into the resulting condensation aerosol for inhalation by the user. However, in other embodiments, the consumable item 217 has aerosol former containing nicotine and other flavourings. In such cases the consumable item 217 typically contains other solid porous matter to absorb the aerosol former liquid, for example a mousse formed with a gelling agent and a suitable binder which may or may not contain tobacco.

The consumables module 218 has a detector 219 for detecting the consumable item 217 inserted into the consumables module 218. The detector 219 is operable to identify a type of the consumable item 217 inserted into the consumables module 218 and to determine if the inserted consumable item 217 is appropriate for use in the aerosol generation device 102. In the present embodiment, the consumables module 218 achieves this by detecting an indicium (e.g. a printed bar code or an RFID chip or an NFC tag etc.) on the consumable item 217.

In an alternative embodiment, the consumable item 217 is a capsule containing aerosol former stored in a reservoir and having a vaporisation chamber whereby liquid from the reservoir is heated by the heating element 216 (e.g. via a wick or via a heat transfer element or via a dosing element which transports a small dosage of liquid aerosol former to a heated vaporisation surface which is heated by the heating element 216, etc.). Preferably the aerosol former comprises VG or a PG/VG mixture together with nicotine and/or flavourings.

In another alternative embodiment, the aerosol generation device 102 does not include the heating element 216, but instead provides power to the consumable item 217, which itself contains a heating element (e.g. the consumable item is a "cartomiser"). In such case the cartomiser includes a liquid reservoir for storing the aerosol former, which is again preferably formed of VG or a PG/VG mixture together with nicotine and/or flavourings.

It is also possible that the aerosol generation device 102 further includes a capsule downstream of the cartomiser or vaporisation chamber, which capsule contains processed tobacco granules which impart flavour and/or nicotine to the condensation aerosol as it passes through the capsule before exiting the aerosol generation device 102 for inhalation by a user.

The aerosol generation device 102 is configured to run a plurality of software modules. The software modules include an operating system 226, a short-range wireless communication controller 228 and a heating element controller 230. Each of the software modules comprises a set of instructions for performing one or more functions of the aerosol generation device 102. The instructions are provided in the form of computer executable code stored in the storage 206 and/or the memory 204, and processed by the CPU 202, communication interface 208 and user interface 212.

In the present embodiment, the operating system 226 is an embedded or a real time operating system. Such operating systems are optimised to reduce delays and to allow for a better user experience. The operating system 226 manages the basic functioning of the hardware of the aerosol generation device 102 and operational interactions between the hardware components of the aerosol generation device 102 and software modules.

The short-range wireless communication controller 228 is primarily configured to control the communication interface 208. It is operable to establish the short-range wireless connection via the communication interface 208. In the present embodiment, the short-range wireless communication connection is a Bluetooth® connection. Consequently, the short-range wireless communication controller 228 includes instructions in accordance with the Bluetooth® wireless communication standards, as available at www.bluetooth.org, with Bluetooth 5.0 being the currently prevailing specification.

The heating element controller 230 is configured to control the heating element 216. It is operable to monitor the amount of energy and the power (i.e. rate of energy) supplied to the heating element 216 and the temperature of the heating element 216 (preferably by monitoring the resistance of the heating element 216, which is known to vary in a predetermined way with the temperature of the heating element 216). In particular though, in the present embodiment, the heating element controller 230 is configured to receive commands to disable or enable the use of the heating element 216. (Note that in embodiments where the aerosol generation device 102 does not itself include a heating element 216 but instead supplies power to a heating element within a consumable item 217 (e.g. a cartomiser) then the heating element controller 230 instead controls the supply of power to the heating element contained within the consumable item 217).

Figure 3:
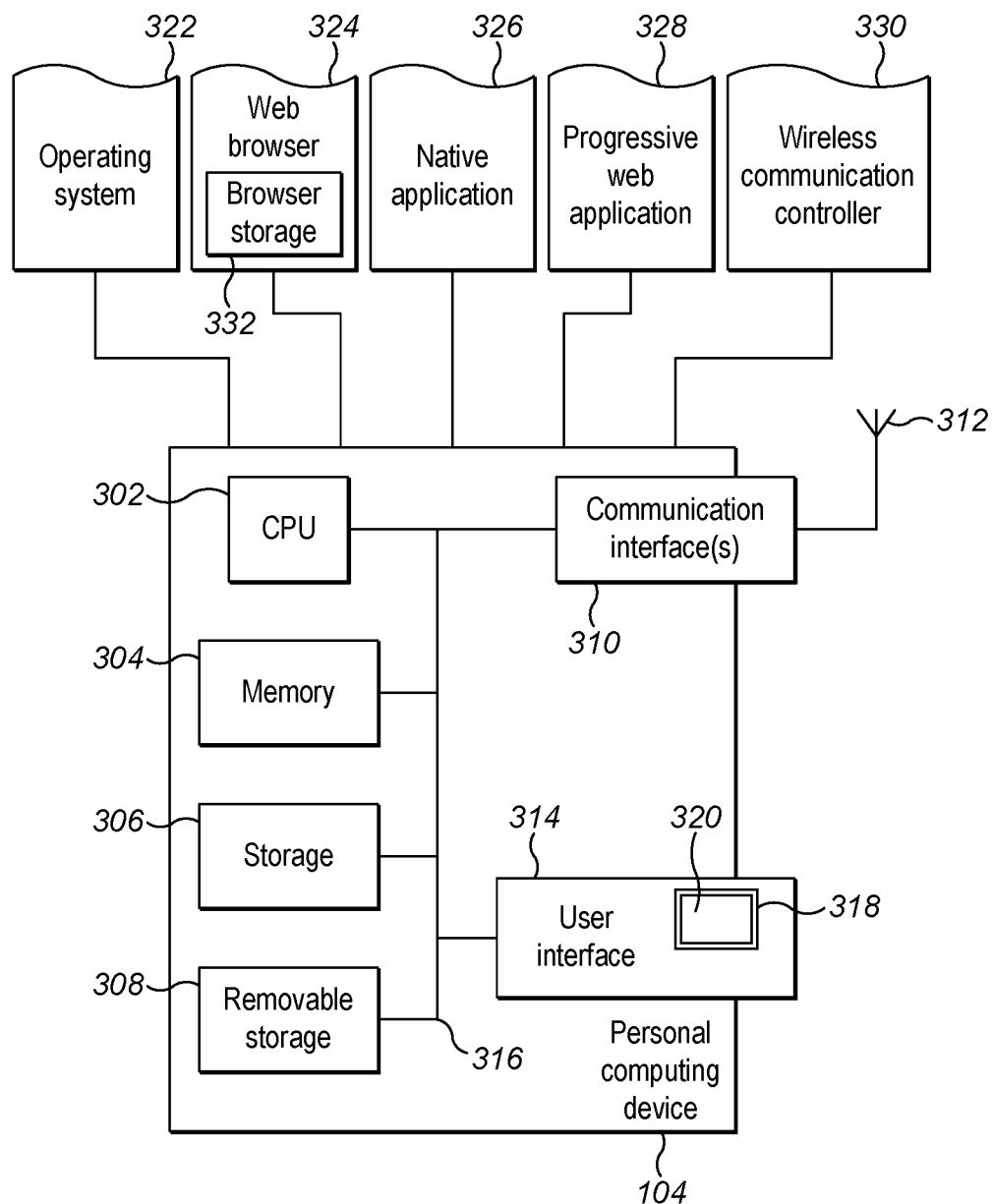
FIG. 3 is a schematic diagram of a personal computing device operating in the communication network.

Referring to FIG. 3, the personal computing device 104 comprises a CPU 302, memory 304, storage 306, removable storage 308, communication interface 310, antenna 312 and user interface 314 in communication with one another via a communication bus 316.

The CPU 302 is a computer processor, e.g. a microprocessor. It is arranged to execute instructions, e.g. in the form of computer executable code, and to process data, e.g. in the form of values or strings, including instructions and data stored in the memory 304, storage 306 and removable storage 308. The instructions and data executed and processed by the CPU 302 include instructions and data for coordinating operation of the other components of the personal computing device 104, such as the communication interface 310 and the user interface 314. They also include instructions and data for running applications on the personal computing device 104.

The memory 304 is implemented as one or more memory units providing RAM for the personal computing device 104. In the illustrated embodiment, the memory 304 is a Dynamic RAM (DRAM) memory chip integrated on a motherboard of the personal computing device 104 alongside the CPU 302. However, in other embodiments, the memory 304 is provided differently, for example in an integrated package with the CPU 302 or as plug-in memory unit. The memory 304 is arranged to store the instructions and data executed and processed by the CPU 302. Typically, only selected elements of the instructions and data are stored by the memory 304 at any one time, the selected elements defining the instructions and data relating to the operations of the personal computing device 104 being carried out at the particular time. In other words, the instructions and data are stored transiently in the memory 304 whilst some particular process is handled by the CPU 302.

The storage 306 is provided integrally with the personal computing device 104, in the form of a non-volatile memory. The storage 306 comprises a memory unit, usually including a Read Only Memory (ROM), flash memory and or a cache memory, integrated on the motherboard of the personal computing device 104. Removable storage 308 is also provided in the illustrated embodiment, although this is optional. The removable storage 308 is again a non-volatile memory, typically in the form of a micro Secure Digital (SD) card or some other portable flash memory device. The storage 306 and removable storage 308 are arranged to store the instructions and data used by the personal computer device 104. The storage 306 and removable storage 308 stores the instructions and data permanently or semi-permanently, e.g. until overwritten. Typically, the elements of the computer instructions and data stored by the storage 306 and removable storage 308 comprise instructions and data essential to basic operation of the personal computing device 104, as well as instructions and data relating to applications installed or installable on the personal computing device 104, including those that perform the methods described below.

The communication interface 310 comprises a short-range wireless communications interface and a cellular radio communications interface, and is coupled to the antenna 312. The short-range wireless interface is configured to establish the short-range wireless communication 116, for example the Bluetooth® connection, with the aerosol generation device 102, and to establish the other short-range wireless communication connection 118, for example the Wi-Fi® connection, with the access point 110. The cellular radio communications interface is configured to establish the cellular radio communication connection 120 to the Internet 112 using appropriate protocols previously discussed. As such, the communications interface 210 comprises one or more wireless modems suitable for supporting the different communication connections 116, 118, 120 (see FIG. 1). In another embodiment, the communication interface 310 also comprises a wired communication interface. The wired communication interface may be used to provide a wired communication connection, for example an Ethernet or Universal Serial Bus (USB) connection (not shown), to the access point 110.

The user interface 314 comprises a display 318 and an input device 320. In the present embodiment, the display 318 and the input device 320 are implemented together as a touch sensitive screen. The display 318 is a Thin-Film-Transistor (TFT) Liquid Crystal Display (LCD) display or an Organic Light Emitting Diode (OLED) display, or other appropriate display. The input device 320 is a capacitive layer provided over the display 318, arranged to detect touch by the user. The user interface 314 is arranged to display information to the user under the control of the CPU 302 and to convey input from the user, derived from the user touching the input device 320, to the CPU 302 via the communication bus 316.

The personal computing device 104 is configured to run a plurality of software modules. The software modules include an operating system 328, a web browser 324, a native application 326, Progressive Web Application (PWA) 328 and a wireless communication controller 330. Each of the software modules comprises a set of instructions for performing one or more functions of the personal computing device 104. The instructions are provided in the form of computer executable code stored in the storage 306, removable storage 308 and/or the memory 304, and processed by the CPU 302, communication interface 310 and user interface 314.

In the present embodiment, the personal computing device 104 is a smartphone whose operating system 322 is an Android® operating system. However, several other operating systems are suitable as alternatives, such as Apple® iPhone® OS (iOS) and Microsoft® Windows® 10. The operating system 322 manages the basic functioning of the hardware of the personal computing device 104 and operational interactions between the hardware components of the personal computing device 104 and software modules.

The web browser 324 is configured to download and process web resources from the Internet 112, and to render them on the display 318 where appropriate. The web browser 324 is also configured to cache downloaded web resources in the memory 304 and storage 306 of the personal computing device 104. Typically, the web browser 324 downloads HyperText Markup Language (HTML), JavaScript, Cascading Style Sheet (CSS), and image files. These web resources are processed to display information, such as web pages, on the display 318 of the user interface 314. In the present embodiment, the web browser 324 is Google® Chrome®, but this is not essential and in other embodiments the web browser is, e.g., Safari®, Firefox® or Microsoft® Edge®. Alternatively, the web browser 324 may be a web browser designed specifically for handling PWAs, offline web pages, or other web based technologies, such as Electron™ developed by GitHub®.

The web browser 324 has browser storage 332. Physically, the browser storage 332 is effectively a part of the memory 304 or storage 306. However, more importantly, the operating system 322 and web browser 324 are configured to provide the browser storage 332 as a portion of memory having certain operating characteristics. Specifically, browser storage 332 is storage in which stored data persists after a session of the web browser 334 ends or after the web browser 334 stops its execution. In some embodiments, browser storage 332 is implemented as web storage, as the term is understood under, say, the Hypertext Markup Language 5 (HTML5) standard. More specifically, the browser storage 332 is local storage. Local storage data (unlike cookies) is not automatically transmitted to a web server in every request or interaction with the web server and cannot be written to directly by the web server. Local storage is distinguished from session storage, which is per-origin-per-window-or-tab and does not persist after the session is over, or the tab or window closed. Local storage is available, for example, in HTML5. The browser storage 332 is, in this embodiment, stored within files of the web browser 334 (e.g. files storing user preferences and other configurations, etc.).

The native application 326 is configured to manage running of the web browser 324 and the PWA 328. In particular, the native application 326 is arranged to modify the functionality of the web browser 324 so that it can handle calls made by the PWA 328 for communication to the aerosol generation device 102 via the short-range wireless communication connection 116. In the present embodiment, this is achieved by the native application 326 providing a resource, e.g. code such as Javascript and/or Swift code. The resource specifies how calls generated within the web browser 324 by the PWA 328, e.g. using a Web Bluetooth® Application Programming Interface (API), should result in corresponding commands processed by the native application 326, e.g. using a Bluetooth® API. The commands are configured to cause the wireless communication controller 320 to perform certain operations, e.g. setting up the short-range wireless communication connection 116 (e.g. a Bluetooth® connection) or transmitting or receiving messages over the short-range wireless communication connection 116. In this way, the native application 326 provides seamless communication between the PWA 328 and the wireless communication controller 330.

It will be appreciated that the native application 326 generally has access to hardware and peripherals of the personal computing device 104 via the operating system 322. The hardware and peripherals include the communication interface 310, storage 306, removable storage 308 and user interface 314, as well as cameras, microphones etc. (not shown). The native application 326 can therefore provide communication between the PWA 328 and other hardware and peripherals of the personal computing device 104, not just the communication interface 310.

The native application 326 is typically programmable using a Software Development Kit (SDK). By using the appropriate SDK, it is possible to configure the native application 326 to have the functionality described above. In particular, it possible to configure the native application 326 to interface with the operating system 322 and the appropriate software drivers so as to control the hardware and peripherals of the personal computing device 104 as required, and to provide the resource to the web browser 324.

The web browser 324 is configured to download, store, and run the PWA 328. The PWA 328 typically comprises HyperText Markup Language (HTML), JavaScript, Cascading Style Sheet (CSS), JavaScript Object Notation (JSON), eXtensible Markup Language (XML), image files or any other files of the PWA 328. The files of the PWA 328, e.g. in the form of instructions and data, are initially downloaded from the web server 422 of the remote server 114 and thereafter stored in the browser storage 332. In an alternative embodiment, the files of the PWA 328 are stored elsewhere in storage 306, memory 304, and/or a cache of the CPU 302.

In general, PWAs provide a way for users to benefit from similar functionality to that provided by native applications. However, PWAs are limited in that they cannot necessarily access certain functions, data structures and interfaces of the personal computer devices on which they may run. For example, ways of accessing some functions, data structures and interfaces of the personal computer device 104 are defined in the SDK for the native application 326, and are not accessible via the web browser 324 on which the PWA 328 runs. In some instances, indirect access to certain hardware and peripherals is still possible to for PWAs via through Web APIs. However, there are many exceptions to this, and the utility of Web APIs varies from device to device. In particular, even though the PWA 328 is configured to receive messages or data received at the personal computing device 104 via the Web Bluetooth® API and similarly to transmit messages or data to the aerosol generation device 102 connected to the personal computing device 102 via the Bluetooth® Web API, this will not be effective unless the personal computing device 102 is configured to function with the Web Bluetooth® API. This configuration is provided by the native application 326.

The wireless communication controller 330 is primarily configured to control the communication interface 310. It is operable to establish the short-range wireless connection 116 via the communication interface 310. In the present embodiment, the short-range wireless communication connection 116 is a Bluetooth® connection. Consequently, the wireless communication controller 330 includes instructions in accordance with the Bluetooth® wireless communication standards, as available at www.bluetooth.org, with Bluetooth 5.0 being the currently prevailing specification.

The wireless communication controller 330 includes any necessary hardware drivers for controlling the Bluetooth® module (which is part of the communication interface 310) as well as the Android® Bluetooth® API by which the native application 326 can access and control the Bluetooth® module of the communication interface 310 (e.g. in response to a call to the Web Bluetooth® API by the PWA 328).

Figure 4:
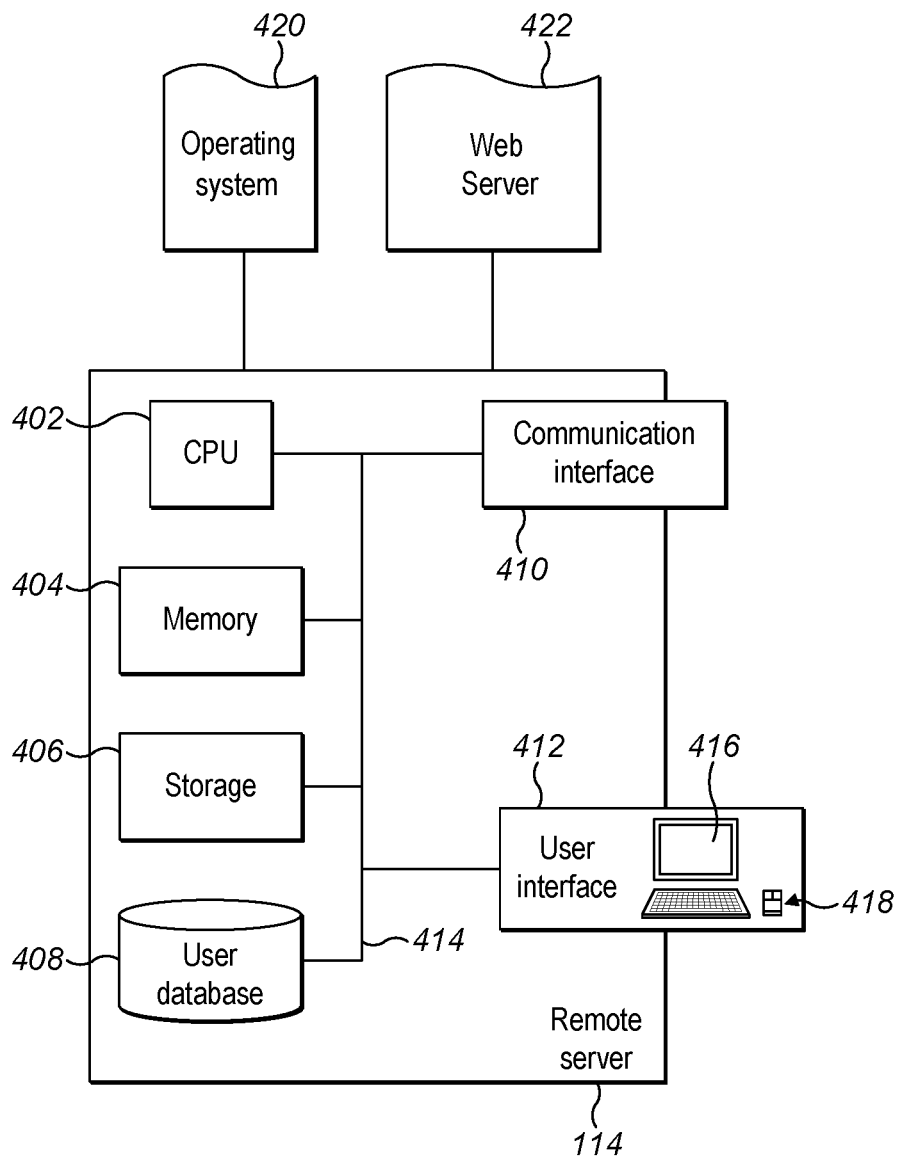
FIG. 4 is a schematic diagram of a remote server operating in the communication network.

Referring to FIG. 4, the remote server 114 comprises a CPU 402, memory 404, storage 406, a user database 408, communication interface(s) 410 and user interface 412 in communication with one another via a communications bus 414.

The CPU 402 is a computer processor, e.g. a microprocessor. It is arranged to execute instructions, e.g. in the form of computer executable code, and to process data, e.g. in the form of values and strings, including instructions and data stored in the memory 404 and storage 406. The instructions and data executed and processed by the CPU 402 include instructions and data for coordinating operation of the other components of the remote server 114, such as the user database 108, communication interface 410 and user interface 412. They also include instructions and data for running applications on the remote server 114.

The memory 404 is implemented as one or more memory units providing RAM for the remote server 114. In the illustrated embodiment, the memory 404 is a DRAM memory unit mounted to a motherboard of the remote server 114 alongside the CPU 402. However, in other embodiments, the memory 404 is provided differently, for example as a memory chip integrated with the motherboard or the CPU 402. The memory 404 is arranged to store the instructions and data executed and processed by the CPU 402. Typically, only selected elements of the instructions and data are stored by the memory 404 at any one time, the selected elements defining the instructions and data relating to the operations of the remote server 114 being carried out at the particular time. In other words, the instructions and data are stored transiently in the memory 404 whilst some particular process is handled by the CPU 402.

The storage 406 comprises a hard disk drive or flash drive mounted in the remote server 114 or as a separate storage unit accessible to the remote server 114. The User database 408 may be implemented with the storage. That is, the user database 408 is typically a part of the storage 406, e.g. data stored by the storage. However, in other embodiments, the user database 408 is separate from the storage, e.g. comprising a separate hard disk drive or storage unit. The storage 406 is arranged to store the instructions and data used by the remote server 114. The storage 406 stores the instructions and data permanently or semi-permanently, e.g. until overwritten. Typically, the elements of the instructions and data stored by the storage 406 comprises instructions and data essential to basic operation of the remote server 114, as well as instructions and data relating to applications installed or installable on the remote server, including those that perform the methods described below. The user database 408 is configured to store information relating to users that own, or have owned, one or more of the aerosol generation device(s) 102, along with configuration information relating to the users and the aerosol generation devices 102.

The communications interface 410 comprises a wired communication interface that is configured to connect to the Internet 112. The wired communication interface typically connects to the Internet 112 via an access point (not shown) and an Internet Service Provider (ISP), for example via an Ethernet or Universal Serial Bus (USB) connection (not shown), and a suitable modem.

The user interface 412 comprises a display 416 and an input device 418. In the present embodiment, the display 416 is a computer monitor and the input device 418 is a keyboard and mouse.

The remote server 114 is configured to run a plurality of software modules. The software modules include an operating system 420 and a web server 422. Each of the software modules comprises a set of instructions and data for performing one or more functions of the remote server 114. The instructions, e.g. provided in the form of computer executable code, and the data, e.g. in the form of values or strings, are stored in the memory 404 and storage 406, and executed or processed by the CPU 402.

In the present embodiment, the operating system 420 is a server optimised operating system, such as those provided by Linux® and Microsoft® Windows®. The operating system 420 manages the basic functioning of the hardware of the remote server 114 and operational interactions between the hardware components of the remote server 114 and the software modules. In some embodiments, the web server 422 is implemented as part of the operating system 420, e.g. as a function or module of the operating system 420. In other embodiments, the web server 422 is an application running on the remote server 114, or even at a remote site under the control of the remote server 114. The web server 422 is arranged to provide the files for running the PWA 328 to the personal computing device 104, on request. It also provided a portal to manage interactions between the personal computing device 104 (and aerosol generation devices 102) and the user database 408.

Figure 5:
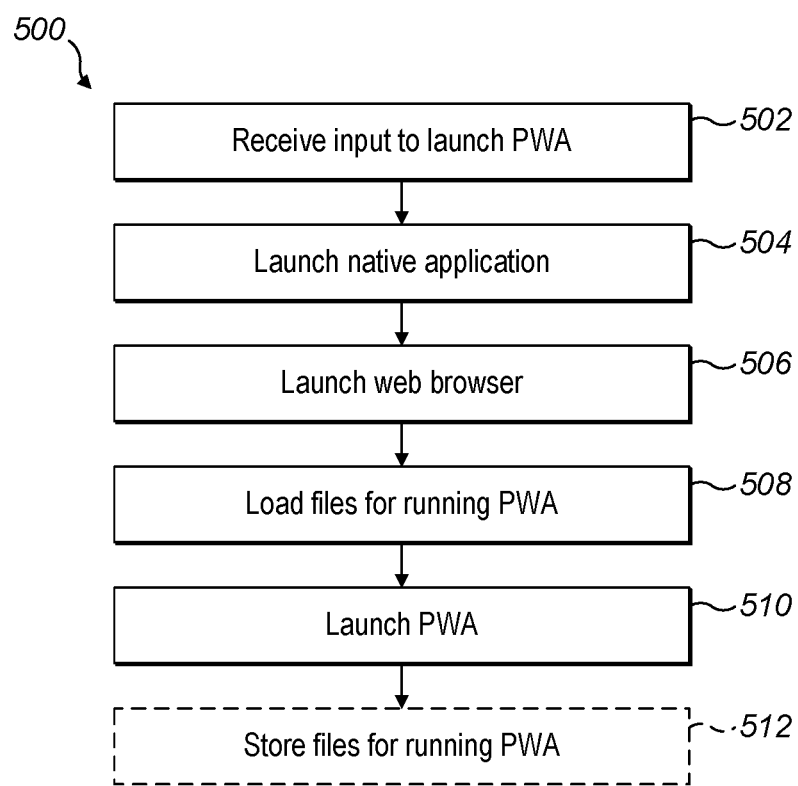
FIG. 5 is a flow diagram illustrating a method of preparing and launching a Progressive Web Application (PWA) on the personal computing device.

Referring to FIG. 5, a method 500 of launching the PWA 328 involves a user first interacting with the user interface 314 of the personal computing device 104 to provide an input indicating that the user wishes to open the PWA 328. In one embodiment, when the user first purchases an aerosol generation device 102, the user is prompted to download and install the PWA 328. In this embodiment, the user accesses a URL that is present on the packaging or user interface 212 of the aerosol generation device 102 using the web browser 324 of the personal computing device 104. The URL points to a website hosted on the web server 422 of the remote server 114. In one embodiment, the accessing of the URL is achieved by the user operating the personal computing device 104 to scan a barcode that encodes the URL. Specifically, the barcode may be a 2D barcode. Alternatively or in addition, the URL is presented in plain text for the user to type into the web browser 324 of the personal computing device 104.

In more detail, the user is typically prompted by the packaging of the newly purchased aerosol generation device 102 to visit a specified website associated with the personal computing device 104. At the website the user is given instructions as to how to download the native application 326 from a suitable repository for whichever type of operating system the user's personal computing device 104 is employing (e.g. Android®). Once the user follows these instructions and downloads and installs the native application 326 the user is asked to launch the native application 326 and from within the native application 326, or more specifically from within the web browser 324 launched under the control of the native application, to navigate to a specified website from whence the PWA 328 is downloaded. From within the native application 326, the downloading of the PWA 328 may commence automatically once the URL is selected, or following a further input from the user, e.g. by the user double clicking on an associated icon on the user interface 314 of the personal computing device 104. When the PWA 328 has not previously been accessed from the particular personal computing device 104 and/or is not installed on the personal computing device 104, the icon may be displayed in the web browser 324. That is, the user first navigates to a web page provided to the personal computing device 104 by the web server 422, which web page includes the icon. Once the files for running the PWA 328 have been downloaded from the web server 422, the PWA may be launched.

During subsequent launches of the PWA 328, the icon is typically displayed on a home screen element of the personal computing device 104. When this icon is selected by the user, the personal computing device 104 receives, at step 502, an input indicating that the user wishes to launch the PWA 328. In response to the input from the user, rather than launching the PWA 328 directly, the personal computing device 104 launches the native application 326 on the personal computing device 104, at step 504. The native application 326 in turn launches (or re-launches) the web browser 324, at step 506. The native application 326 then loads files for launching the PWA 328, at step 508, and launches the PWA 328 on the web browser 324, at step 510.

It will be understood that the native application 326 allows a user to initiate the launching of the PWA 328 via the user interface 314 using the method. However, in some embodiments, the native application 326 automatically (i.e. without explicit interaction from the user) causes the PWA 328 to be launched, particularly for second and subsequent launchings of the PWA 328, where the files for running the PWA 328 are already downloaded and stored (cached) in the browser storage 324 of the web browser 324. In such a case, it is preferred that the user has some way of preventing the automatic launching of the PWA 328 if they should choose to do so, e.g. by clearing from the browser storage 324 the stored files necessary for running the PWA 328 or by modifying a setting associated with the native application 326 or by some other suitable mechanism.

In order to launch the PWA 328, the native application 326 first launches the web browser 324, at step 506. More specifically, rather than launching the web browser 324 in a standard way on the personal computing device 102, e.g. as if the user had initiated launch of the web browser 324 themselves, the native application 326 launches the web browser 324 in a modified way. Specifically, the native application 326 launches the web browser 324 with suitable functionality for supporting the PWA 328. This includes native application 326 adding resources to the web browser 324 in the form of JavaScript code (or in other embodiments Python or another suitable computer language). The resources are generally part of the software of the native application 326. In other embodiments, they may be stored at the web server 422 and accessed by the native application 326, e.g. when the PWA 328 is downloaded from the web server 422. The resources may be specific to the operating system 322 of the personal computing device 104, e.g. the resources provided for Android® may be different to the resources provided for iOS®. The resources are added to libraries of the web browser 324 as objects. More specifically, they are added as part of the Document Object Model of the PWA 328.

The PWA 328 is launched on the web browser 324, at steps 508 and 510, by the web browser 324 being directed to the Uniform Resource Locator for the PWA 328. If it is the first time the web browser 324 is opening the URL, the web browser 324 uses the URL to download the files for running the PWA 328 from the remote server 114. The files for running the PWA 328 are received from the remote server 114 via the Internet 112. In the present embodiment, the files for running the PWA 328 are received over the long-range communication connection 120 from the remote server 114. In an alternative embodiment, the files for running the PWA 328 are received over the short-range wireless communication connection 118 with the access point 110. Once the web browser 324 downloads the required files, the web browser 324 launches the PWA 328, at step 510, and stores the files for running the PWA 328 in the browser storage 332 of the web browser 324, at step 512. In other embodiments, the files required for the PWA 328 are stored elsewhere in the storage 306 of the personal computing device 104.

If the PWA 328 (e.g. the set of files required for the PWA 328) has been downloaded already, the web browser 324 retrieves the files for running the PWA 328 from the browser storage 332 or elsewhere in the storage 306 or memory 304 of the personal computing device 104. In this scenario, the files do not need to be stored again, and step 512 is therefore shown as optional in FIG. 5.

The files for running the PWA 328 include any one or more of the following files: HyperText Markup Language (HTML), JavaScript, Cascading Style Sheet (CSS), JavaScript Object Notation (JSON), eXtensible Markup Language (XML), images, or any other PWA related files. These files may be compressed and require decompression. The files for running the PWA 328 may be minified and/or obfuscated.

Figure 6A:
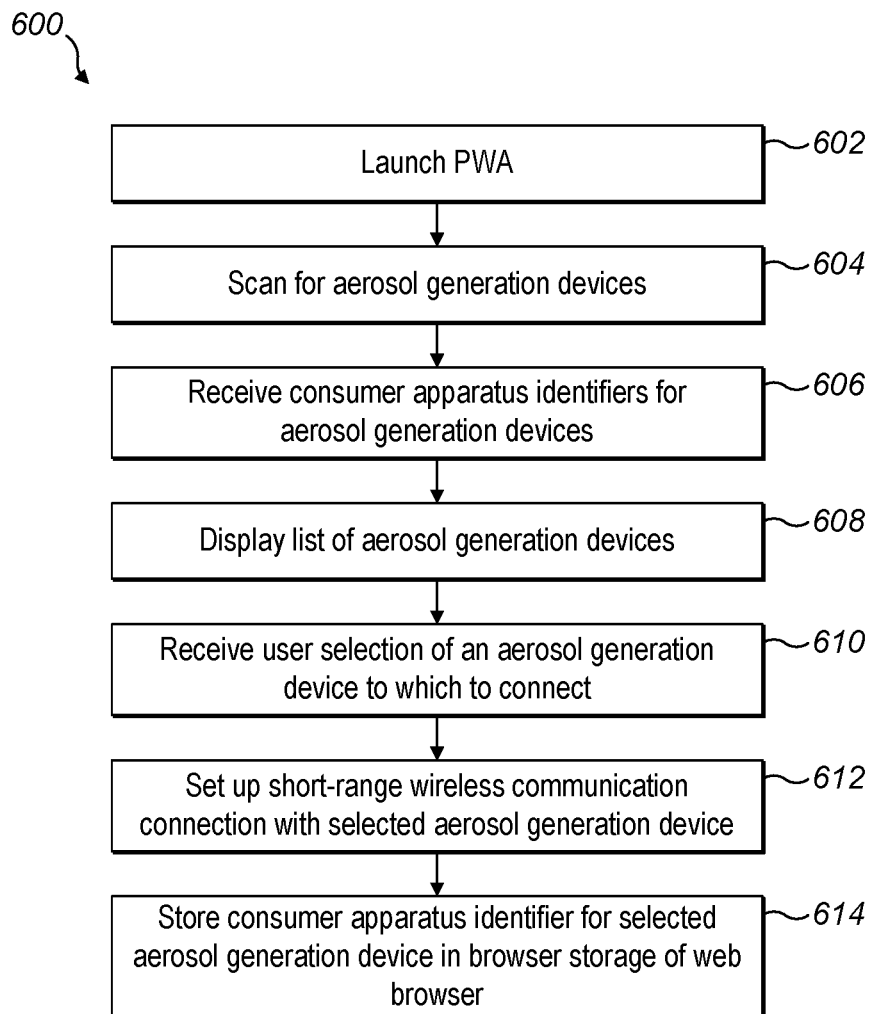
FIG. 6A is a flow diagram illustrating a method of establishing a short-range wireless communication connection between the personal computing device and the aerosol generation device.
Figure 6B:
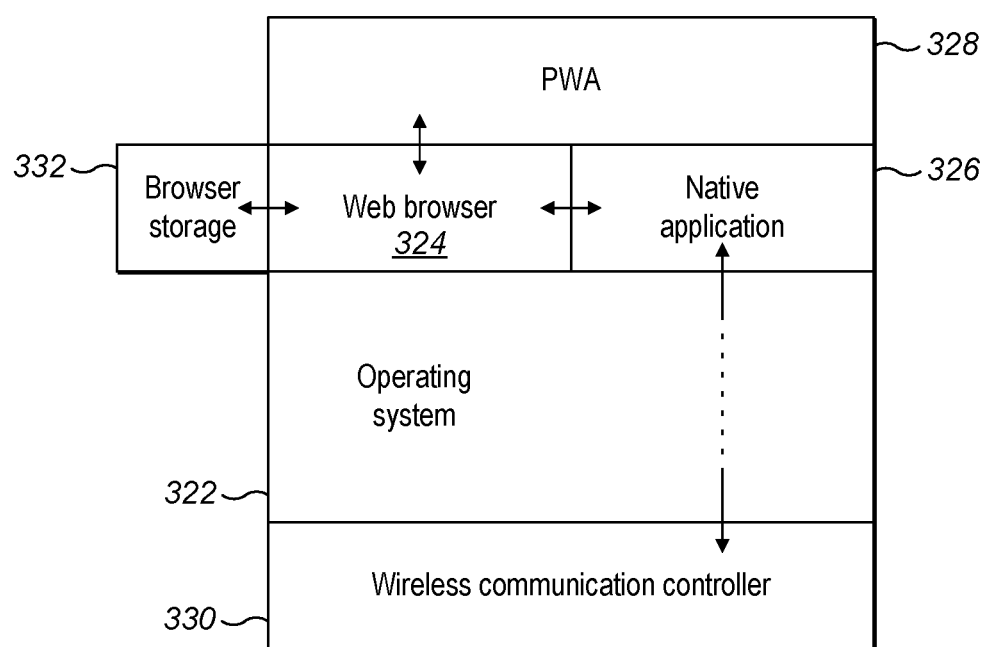
FIG. 6B is a schematic illustration of software layers on the personal computing device.

Referring to FIGS. 6A and 6B, a method 600 of establishing the short-range wireless communication connection 116 with one of the aerosol generation devices 102 and storing configuration information of aerosol generation device 102 comprises first launching the PWA 328, at step 602, using the method 500 of launching the PWA 328 described with reference to FIG. 5 above. Using the PWA 328, the user then initiates a command to scan for nearby aerosol generation devices 102, at step 604. The user initiates the command to scan for nearby aerosol generation devices 102 by interacting with the PWA 328 via the user interface 314 of the personal computing device 104. In this embodiment, the user initiates the scanning by selecting an icon within the PWA 328 displayed by the web browser 324. In alternative embodiments, the PWA 328 scans for aerosol generation devices 102 when the PWA 328 starts, at a certain time after the PWA 328 has started, periodically, at a set time in the day, when a timer triggers, when requested by the remote server 114, or when requested by the aerosol generation device 102.

The PWA 328 provides a call to initiate the scanning. In this embodiment, the PWA 328 uses a web browser short-range wireless communication function, e.g. the Web Bluetooth® API, to generate the call. The call may comprise JavaScript® roughly as follows:

```
navigator.bluetooth.requestDevice(options)
// Connect GATT server
.then (device => {
    log('> Name:            ' + device.name);
    log('> Id:              ' + device.id);
    log('> Connected:       ' + device.gatt.connected);
    return device.gatt.connect( );
})
```

Such a call would routinely be rejected by the web browser 324, as the web browser 324 does not inherently include functionality for communicating with the wireless communication controller 330. However, using the functionality added to the web browser 324 by the native application 326 when the native application 326 launched the web browser 324, the web browser 324 in its modified form, is able to respond to the call.

In more detail, the code causes the web browser 324 to access the object found in its directory at "navigator.bluetooth.requestDevice". In this embodiment, that object is JavaScript previously inserted by the native application 326 when the web browser 324 was launched. This code may comprise JavaScript® roughly as follows:

```
navigator.bluetooth = {
requestDevice: function(options) {
    var id = window.guid( );
    var p = new Promise(function(resolve, reject) {
        window.promises[id] = {
            resolve: resolve,
            reject: reject
        };
    });
    var message = {
        messageId: id,
        fn: 'requestDevice',
        parameters: options
    };
    var messageString = JSON.stringify(message);
    window.webkit.messageHandlers.notification.postMessage
    (messageString);
    return p;
}
```

So, when the PWA 328 generates the call to scan for aerosol generation devices 102, the web browser 324 processes the call using the object found in its directory at the appropriate location, e.g. using the code above. This code functions to provide a promise to the web browser 324. It also causes the web browser 324 to provide swift code to the native application 326. So, the web browser 324 effectively converts the call into a command to the native application 326. The swift code defining the command to the native application 326 may be roughly as follows:

```
let messageBody = message.body as! String
if let dataFromString = messageBody.data(using: .utf8,
allowLossyConversion:
false) {
    do {
        let json = try JSON(data: dataFromString)
        try self.processJsonMessage(json: json)
    } catch {
    }
}
```

The native application 326 receives the command and uses it to initiate the wireless communication controller 330 to scan for aerosol generation devices 102. Upon receipt of the command, the native application 326 executes the following code with the wireless communication controller 330:

```
case "requestDevice":
    var uuidServices = [CBUUID]( )
    var deviceName: String?
    if let filters = json["parameters"]["filters"].array {
        for filter in filters {
            if let name = filter["name"].string {
                deviceName = name
            }
        }
    }
```

```
        if let services = filter["services"].array {
            uuidServices         =         services.map        {        CBUUID(string:
$0.stringValue.uppercased( )) }
        }
      }
    }
    if let acceptAllDevices = parameters["acceptAllDevices"].bool {
      if acceptAllDevices {
        uuidServices = [ ]
        deviceName = nil
      }
    }
  }
  print("Scan started for:")
  print(" - Services: \(uuidServices)")
  print(" - Device name: \(deviceName)")
  self.delegate?.startedScanning(name: deviceName, services: uuidServices)
  let scanFuture = self.manager.startScanning(forServiceUUIDs: nil)
  scanFuture.flatMap { [weak manager]  discoveredPeripheral        ->
FutureStream<Void> in
    self.delegate?.foundPeripheral(discoveredPeripheral)
    return FutureStream<Void>( )
  }
```

This causes the wireless communication controller 330 to control the communication interface 310 of the personal computing device 104 to scan for aerosol generation devices 102, at step 604. Any aerosol generation devices 102 that are within range, in a discoverable mode (or that are already paired to the personal computing device 104), and also have short-range wireless communication interfaces of the same protocol as the personal computing device 104 respond. The aerosol generation devices 102 respond with configuration information, comprising a consumer apparatus identifier. In the present embodiment, the consumer apparatus identifier is the Bluetooth® Media Access Control (MAC) address of the aerosol generation device 102.

The configuration information of each aerosol generation device 102 is received at wireless communication controller 330 of the personal computing device 104 and then sent to or retrieved by the PWA 328, at step 606. More specifically, the native application 326 receives a response from the wireless communication controller 330 that, in the present embodiment, comprises swift code roughly as follows:

```
func notify(uuid : String, contents : String) {
    let message ToSend = "window.notify('\uuid)', \(contents))"
    self.webView.evaluateJavaScript(messageToSend) { (any, error) in }
}
```

It will be apparent that the PWA 328 makes calls to the Web Bluetooth® API in order to carry out tasks such as scanning for devices over the short-range wireless communication connection 116, or writing or receiving messages or data to and from the aerosol generation devices 102. In the present embodiment this is done in a manner which is agnostic as to which application is actually supporting the Web Bluetooth® API—i.e. the (unmodified) web browser 324 or the web browser 324 when appropriately modified by the native application 326. Preferably therefore the native application 326 is configured to determine if the web browser 324 can handle Web Bluetooth® API calls (in the desired manner) in which case it does not need to apply the code for modifying the web browser 324 to be able to handle Web Bluetooth® API calls (unless it needs them to be handled in a non-standard way for some reason in which case it can still modify the web browser 324 by effectively over-riding the standard functions for handling Web Bluetooth® API calls to perform the desired non-standard actions). This functionality is preferably handled by having the native application 326 query the web browser 324 for its name and version and comparing this with a look up table which specifies the correct actions to take (in terms of to what extent to modify the existing behaviour of the web browser 324) depending on the name and version of the web browser 324, the operating system 322 or of the personal computing device 104 itself.

With all of the configuration information of the aerosol generation device(s) 102 received 610, the personal computing device 104 displays a list of all of the candidate aerosol generation devices 102 on the user interface 312, at step 608.

A user selects which of the candidate aerosol generation devices 102 they would like to interact with. One or more may be selected. (Note, in an alternative embodiment, if only one aerosol generation device 102 is identified as being in range and it is one which the user has previously selected from the PWA 328, then the PWA 328 can automatically select that aerosol generation device 102 without requiring confirmation from the user thus effectively skipping displaying the list and receiving user selection and moving instead directly from receiving configuration information 610 to setting up the short-range wireless communication connection 116 with the aerosol generation device 102 as now described in greater detail below). The selection is received at the user device 102, at step 610.

The PWA 328 causes the personal computing device 104 to open the short-range communication connection 116 with the selected aerosol generation device 102, at step 612. The short-range wireless communication connection 116 is set up using some or all of the configuration information for the selected aerosol generation device(s) 104. In the present embodiment, the consumer apparatus identifier is used to set up the short-range wireless communication connection 116. In this example, the MAC address of the selected aerosol generation device(s) 102 is the consumer apparatus identifier.

Further configuration information may comprise any one or more of the following information indicative of the functioning of the aerosol generation device 102:
Generic Attribute Profile Services (GATT) information,
GATT UUIDs,
GATT Characteristics, authentication information,
capsule information,
device settings,
event information, and/or
vaping information.

Capsule information, which is relevant in embodiments in which the aerosol generation device 102 takes a consumable item 217 in the form of a capsule or atomiser containing a reservoir of e-liquid to be vaporised, comprises an estimated number of puffs left in capsule and may include amount of e-liquid and/or nicotine left in the capsule. The capsule information is updated regularly, e.g. after every puff and/or when a user changes capsule, etc.

In this embodiment, device settings comprise sleep time and max puff duration. Event information comprises malfunction events, over temperature events and dry vape events. Vaping information comprises information about whether the user is using the aerosol generation device 102. It may further include information about duration, temperature, and capsule information.

The native application 326 receives the information indicative of the functioning of the aerosol generation device 102. The information indicative of the functioning of the aerosol generation device 102 is passed from the native application 326 to the PWA 328 via the web browser 324. The information indicative of the functioning of the aerosol generation device 102 is received at the PWA 328 and can be used by the PWA 328. For example, some or all of the information may be displayed to the user by the PWA on display 318 of the user interface 314 of the personal computing device.

The consumer apparatus identifier is stored in the browser storage 332 of the web browser 324 at step 612. All or a portion the information indicative of the functioning of the aerosol generation device 102 may also be stored in the browser storage 332 of the web browser 324. The storing is carried out by the PWA 328 and/or by the web browser 324. In some embodiments, the information is time stamped with the current time.

Referring to FIG. 7, a method 700 of initiating the short-range wireless communication connection 116 between the personal computing device 104 and the aerosol generation device 102 is shown. For example, after the short-range wireless communication connection 116 between the personal computing device 104 and the aerosol generation device 102 that has already been established using the method described with reference to FIGS. 6A and 6B has been closed, it can be re-initiated again using the method described with reference to FIG. 7.

First, the PWA 328 is launched on the personal computing device 104, at step 702, using the method 500 of launching the PWA 328 described above with reference to FIG. 5.

The browser storage 332 of the web browser 324 stores one or more consumer apparatus identifiers. The PWA 328 accesses the consumer apparatus identifiers, at step 704, from the browser storage 332. A determination of which aerosol generation device 102 to connect to is then made, at step 706. In the present embodiment, the consumer apparatus identifiers stored in the browser storage 332 are presented to the user on the user interface 312 of the personal computing device 104. The user selects which aerosol generation device 102 they wish to connect to. If there is only one aerosol generation device 102 then that aerosol generation device 102 is selected by the user (or may be selected on behalf of the user automatically).

In the present embodiment, the user interface 310 displays a user friendly name for the aerosol generation device 102 associated with the consumer apparatus identifier, e.g. as an icon. When the user interacts with the name or icon of the aerosol generation device 102, the consumer apparatus identifier associated with the aerosol generation device 102 is selected. In another embodiment, the consumer apparatus identifier is itself displayed.

The consumer apparatus identifier corresponding to the determined or selected aerosol generation device 102 is retrieved by the PWA 328 from the browser storage 332, at step 708. The PWA 328 uses the consumer apparatus identifier to cause the personal computing device 104 to initiate the short-range wireless communication connection 116 with the determined or selected aerosol generation device 102, at step 710. It will be appreciated that the consumer apparatus identifier has endured in the browser storage 332 from when the PWA 328 was last used, via the web browser 324 and the native application 326, to establish the short-range wireless communication connection 116. Even if the web browser 324 and native application 326 are themselves closed, e.g. are terminated or stop running, the consumer apparatus identifier remains in the browser storage. This allows the short-range wireless communication connection 116 to be initiated straightforwardly, without having to retrieve the consumer apparatus identifier from the aerosol generation device 102 again, e.g. by re-establishing the short-range wireless communication connection using the method 600 described with reference to FIGS. 6A and 6B.

In this embodiment, the consumer apparatus identifier is the Bluetooth® MAC address and is used to initiate the short-range wireless communication connection 116. In order to initiate the short-range wireless communication connection 116, the PWA 328 generates a call. The call seeks to cause the personal computing device 104 to establish the short-range wireless communication connection 116 with the aerosol generation device 102. The web browser 324 processes the call using the appropriate object found in its directory at the appropriate location. The code of the object functions to provide a promise to the web browser 324. It also causes the web browser 324 to provide swift code to the native application 326, such that the web browser 324 effectively converts the call into a command to the native application 326. The native application 326 receives the command and uses it to cause the wireless communication controller 330 to open the short-range wireless communication connection 116 with the aerosol generation device 102.

Referring to FIG. 8, a method 800 of transmitting information regarding the functioning of the aerosol generation device 102 to the remote server 114 is shown.

With the short-range wireless communication connection 116 between the personal computing device 104 and the selected aerosol generation device 102 already established and/or initiated, the personal computing device 104 receives from the selected aerosol generation device 102, information indicative of the functioning of the selected aerosol generation device 102 over the short-range wireless communication connection 116, at step 802.

In the present embodiment, the information indicative of the functioning of the selected aerosol generation device 102 may comprise any one or more of the following:
identity and/or type of aerosol generation device 102, such as a model and serial number identifying the aerosol generation device 102,
the type and identity of any consumable item 217 installed in the aerosol generation device 102,
the status of the aerosol generation device 102 and/or of the consumable item 217 (if present) such as the battery level of the aerosol generation device 102 and current settings values of the aerosol generation device 102 (e.g. the target temperature setting or a "vapour volume" level setting) and information about the capacity of the consumable item 217 (e.g. the number of puffs remaining before the consumable item 217 will be considered to have expired, the amount of liquid remaining in the consumable item 217 if it includes a reservoir of liquid and/or details about the amount that the consumable item 217 has been used (see below) and/or information about the usage of the aerosol generation device 102 since a previous point in time since such information was successfully sent to the remote 114 server and/or the PWA 328.

The information indicative of the functioning of the selected aerosol generation device 102 is stored in the browser storage 332 of the web browser 324, at step 804. In the present embodiment, the information indicative of the functioning of the selected aerosol generation device 102 is also transmitted to the remote server 114 via the Internet 112, at step 808. In particular, the information indicative of the functioning of the selected aerosol generation device 102 is transmitted to the remote server 114 via the long-range wireless communication connection 120. In another embodiment, the information indicative of the functioning of the aerosol generation device 102 is transmitted 810 to the remote server 114 via the short-range wireless communication connection 118 via the access point 110.

In the present embodiment, the transmission of the information indicative of the functioning of the selected aerosol generation device 102 is not transferred until a connection to the remote server 114 is determined to be available, at step 806. The determination is made by the personal computing device 104 attempting to contact the remote server 114 via the Internet 112. If a connection to the remote server 114 is determined to be available, the transmission of the information indicative of the functioning of the selected aerosol generation device 102 is transmitted to the remote server 114. Note that in an alternative embodiment, some of the information indicative of the functioning of the aerosol generation device 102 is only transmitted to the personal computing device 104 if and only if the personal computing device 102 has determined that a connection to the remote server 114 is available and has communicated this as part of establishing and/or initiating the short-range wireless communication a connection 116 between the personal computing device 104 and the aerosol generation device 102. This particularly applies to any relatively large amounts of data (e.g. puff data history relating to the usage of the aerosol generation device 102 by a user—which may advantageously contain any one or more of the time and duration of each puff taken by the user, the target temperature setting at which each puff was taken and possibly the location of the aerosol generation device 102 at which each puff was taken). In particular, large batches of data such as these may be stored at the personal computing device 102 only until they have been transmitted to the remote server 114 successfully. Thus an example process flow, in overview, would be: receive at aerosol generation device 102 from personal computing device 104 confirmation that the device 104 has a connection to the remote server 114 available; transmit from apparatus 102 large information batch to the personal computing device 104; forward from personal computing device 104 to the remote server 114 large batch of information; receive confirmation from remote server 114 at the personal computing device 104 that the large information batch has been successfully received; send confirmation from personal computing device 104 to the aerosol generation device 102 that the large information batch has been successfully transmitted to the remote server 114; delete from the aerosol generation device 102 the successfully transmitted large information batch.

In a particularly preferred embodiment, the consumable item 217 is a cartomiser that includes a memory for storing data about the consumable 217, which information includes an identifier of the consumable 217, information about the consumable item 217 and preferably information such as the flavour of the consumable item 217, the nicotine strength of the consumable item 217 (e.g. mentholated tobacco flavour at 18 mg/ml concentration of nicotine) and most preferably includes information about the amount of liquid (estimated) to be remaining available in the consumable item 217 for consumption by a user. Most preferably the information about the amount of liquid estimated to be remaining in the consumable item 217 may be information about the usage of the consumable item 217 (e.g. puffs taken whilst containing the consumable item 217 and information about those puffs such as the settings of the aerosol generation device 102 during the puff, the duration of the puff, the energy consumed by the heating element 216 during the puff, ambient temperature or temperature of the heating element 216, prior to, or at the beginning of, the puff, etc.) which may be aggregated (e.g. total energy consumed by the heating element whilst taking puffs from the consumable item 217, total puff duration of all puffs taken at different target temperatures or at different vapour volume settings, average ambient temperature or heating element temperature prior to or at the beginning of a puff, etc.) to minimise the memory required to store the data. Storing usage data rather than an actual estimated liquid level remaining is advantageous because then the server can estimate from this data how much liquid (or how many puffs) is (or are) remaining in the consumable item 217 using a sophisticated algorithm which may be improved over time or may take into account information from a large number of (possibly aggregated to avoid any issues relating to the misuse of personal information) to provide the most accurate information, etc. rather than relying on say the aerosol generation device 102 to have to perform such an estimation.

In the present embodiment, the personal computing device 104 is further configured to send information for the aerosol generation device 102 to the aerosol generation device 102 via the short-range wireless communication connection 116. The information may include any one or more of the following:

settings for the aerosol generation device 102, such as maximum power levels for the heating element 216,
operation enablement messages,
user authentication information, and
firmware updates for the aerosol generation device 102.

The described embodiments of the invention are only examples of how the invention may be implemented. Modifications, variations and changes to the described embodiments will occur to those having appropriate skills and knowledge. These modifications, variations and changes may be made without departure from the scope of the claims.

The invention claimed is:

1. A method of configuring a personal computing device for communication with an aerosol generation device over a short-range wireless communication connection, the method comprising:

a native application launching a web browser on the personal computing device;

the web browser launching a progressive web application (PWA), on the personal computing device; and the native application providing a resource to the web browser, which resource causes the web browser to process a call received by the web browser from the PWA intended for the aerosol generation device by directing a command based on the call to the native application, the command causing the native application to cause the personal communication device to communicate with the aerosol generation device over the short-range wireless communication connection.

2. The method of claim 1, wherein the resource comprises computer code defining operations of the web browser.

3. The method of claim 1, wherein the command comprises computer code defining operations of the native application.

4. The method of claim 1, wherein the resource is provided as an object of the web browser.

5. The method of claim 1, further comprising providing the resource in a Document Object Model of the PWA.

6. The method of claim 1, wherein the native application causes the personal communication device to communicate with the aerosol generation device over the short-range wireless communication connection by communicating with a wireless communication controller of the personal computing device.

7. The method of claim 1, wherein the short-range wireless communication connection is a Bluetooth® connection.

8. The method of claim 1, wherein the call is for initiating the short-range wireless communication with the aerosol generation device and in response to the call the native application is configured to return a consumer apparatus identifier received from the aerosol generation device to the web browser.

9. The method of claim 8, wherein the consumer apparatus identifier is a Media Access Control address for the aerosol generation device.

10. The method of claim 1, further comprising the web browser launching the PWA using files for the PWA downloaded from a web server or stored locally at the personal computing device, whereby even if the personal computing device does not presently have an internet connection, the PWA can still run.

11. The method of claim 1, wherein the aerosol generation device is an electronic cigarette.

12. The method of claim 1, wherein the personal computing device is a mobile personal computing device.

13. The method of claim 1, further comprising storing instructions and/or data for implementing one or more functions of the PWA in browser storage of the web browser, such that after the web browser has been closed and subsequently relaunched by the native application the web browser can retrieve the instructions and/or data for implementing the one or more functions of the PWA from the browser storage.

14. The method of claim 13, wherein the instructions and/or data for implementing the one or more functions of the PWA comprise(s) information enabling establishment of the short-range wireless communication connection with the aerosol generation device.

15. The method of claim 1, further comprising:

causing the personal computing device to scan for one or more candidate aerosol generation devices using a short-range wireless communication protocol; and receiving a consumer apparatus identifier for each of the one or more candidate aerosol generation devices in the vicinity of the personal computing device.

16. The method of claim 15, wherein the scanning for the one or more candidate aerosol generation devices and preferably wherein the receiving the consumer apparatus identifier(s) for the one or more candidate aerosol generation devices is performed by the native application.

17. The method of claim 16, further comprising sending, from the native application to the PWA, the consumer apparatus identifier(s) for the one or more candidate aerosol generation devices.

18. The method of claim 17, further comprising the PWA causing the personal computing device to establish the short-range wireless communication connection with the aerosol generation device comprises the PWA determining the aerosol generation device with which to establish the short-range wireless communication connection from the one or more candidate aerosol generation devices.

19. The method of claim 18, wherein determining the aerosol generation device with which to establish the short-range wireless communication connection comprises:

causing the personal computing device to display a list of the one or more candidate aerosol generation devices; and receiving a user selection of one of the one or more candidate aerosol generation devices as the aerosol generation device with which to establish the short-range wireless communication connection.

20. The method of claim 19, wherein causing the personal computing device to display the list of the one or more candidate aerosol generation devices on the personal computing device and receiving the user selection of one of the one or more candidate aerosol generation devices as the aerosol generation device with which to establish the short-range wireless communication connection is performed by the native application.

21. The method of claim 1, further comprising receiving, at the personal computing device, from the aerosol generation device, information indicative of the functioning of the aerosol generation device via the short-range wireless communication connection.

22. The method of claim 21, further comprising storing the information indicative of the functioning of the aerosol generation device in the browser storage of the web browser.

23. The method of claim 21, further comprising the personal computing device transmitting the information indicative of the functioning of the aerosol generation device to a remote server.

24. The method of claim 23, further comprising, prior to transmitting the information indicative of the functioning of the aerosol generation device to the remote server:

determining whether a communication connection to the remote server is established at the personal computing device; and in response to determining that the communication connection to the remote server is not established at the personal computing device, causing the communication connection to be set up between the personal computing device and the remote server.

25. The method of claim 1, further comprising sending, from the personal computing device to the aerosol generation device, information for the aerosol generation device via the short-range wireless communication connection.

26. The method of claim 1, further comprising receiving, from the a/the remote server, files for running the PWA.

27. A non-transitory computer-readable medium storing instructions which, when executed by one or more computing devices, cause the one or more computing devices to:
- launch, by a native application executing on the one or more computing devices, a web browser;
- launch, by the web browser, a progressive web application (PWA); and
- provide, by the native application, a resource to the web browser, which resource causes the web browser to process a call received by the web browser from the PWA intended for the aerosol generation device by directing a command based on the call to the native application, the command causing the native application to cause the one or more computing devices to communicate with the aerosol generation device over the short-range wireless communication connection.

28. A personal computing device configured for communication with an aerosol generation device over a short-range wireless communication connection, the personal computing device comprising a processor configured to cause:
- a native application to launch a web browser on the personal computing device;
- the web browser to launch a progressive web application (PWA) on the personal computing device; and
- the native application to provide a resource to the web browser, which resource causes the web browser to process a call received by the web browser from the PWA intended for the aerosol generation device by directing a command based on the call to the native application, the command causing the native application to cause the personal communication device to communicate with the aerosol generation device over the short-range wireless communication connection.

* * * * *